US009261350B2

(12) United States Patent
Rubio Guivernau et al.

(10) Patent No.: US 9,261,350 B2
(45) Date of Patent: Feb. 16, 2016

(54) FLEXIBLE WAVEGUIDES FOR OPTICAL COHERENCE TOMOGRAPHY

(71) Applicant: Medlumics S.L., Madrid (ES)

(72) Inventors: José Luis Rubio Guivernau, Madrid (ES); Eduardo Margallo Balbás, Madrid (ES)

(73) Assignee: Medlumics S.L., Madrid (ES)

( * ) Notice: Subject to any disclaimer, the term of this patent is extended or adjusted under 35 U.S.C. 154(b) by 0 days.

(21) Appl. No.: 14/715,182

(22) Filed: May 18, 2015

(65) Prior Publication Data

US 2015/0247720 A1    Sep. 3, 2015

Related U.S. Application Data

(63) Continuation of application No. 13/761,054, filed on Feb. 6, 2013, now Pat. No. 9,062,960.

(60) Provisional application No. 61/596,085, filed on Feb. 7, 2012.

(51) Int. Cl.
*G01B 9/02* (2006.01)
*G02B 6/122* (2006.01)
(Continued)

(52) U.S. Cl.
CPC ........ *G01B 9/02049* (2013.01); *G01B 9/02091* (2013.01); *G02B 6/1221* (2013.01);
(Continued)

(58) Field of Classification Search
CPC ...... G01B 9/02091; G02B 6/136; G02B 6/08; G02B 6/12; G02B 6/125; G02B 6/12002
USPC .................................................. 356/479, 497
See application file for complete search history.

(56) References Cited

U.S. PATENT DOCUMENTS 5,321,501 A * 6/1994 Swanson et al. .............. 356/479
6,834,027 B1 12/2004 Sakaguchi et al.
(Continued)

FOREIGN PATENT DOCUMENTS

JP      2538099       7/1996
JP      H0 9149878    6/1997
(Continued)

OTHER PUBLICATIONS

Zeng et al., Fabrication of Complex Structures on Nonplanar Surfaces Through a Trasnfer Method, Feb. 2011, Journal of Microelectromechanical Systems, vol. 20. No. 1.*

(Continued)

*Primary Examiner* — Jonathan Hansen
(74) *Attorney, Agent, or Firm* — Sterne, Kessler, Goldstein & Fox P.L.L.C.

(57) ABSTRACT

A system and method for depth-resolved imaging of a sample are presented. The system for depth-resolved imaging of a sample includes a substrate of substantially flexible material, a plurality of waveguides disposed on the substrate, an optical element disposed at a distal end of the plurality of waveguides, and one or more interferometers. Light is collected from the sample through the optical element and plurality of waveguides on the flexible substrate on its path to the one or more interferometers. The interferometers are configured to combine a reference light with the light received by at least a portion of the plurality of waveguides to resolve contributions from one or more depths of the sample. The system further includes a light guiding element coupled between the plurality of waveguides and the one or more interferometers.

20 Claims, 9 Drawing Sheets

(51) Int. Cl.

| | | |
|---|---|---|
| *G02B 6/13* | (2006.01) | |
| *G02B 6/26* | (2006.01) | |
| *G02B 6/32* | (2006.01) | |
| *G02B 6/35* | (2006.01) | |
| *A61B 5/00* | (2006.01) | |
| *G02B 6/06* | (2006.01) | |
| *G02B 6/136* | (2006.01) | |

(52) U.S. Cl.
CPC ............... *G02B 6/13* (2013.01); *G02B 6/262* (2013.01); *G02B 6/32* (2013.01); *G02B 6/3596* (2013.01); *A61B 5/0066* (2013.01); *G02B 6/06* (2013.01); *G02B 6/136* (2013.01)

(56) References Cited

U.S. PATENT DOCUMENTS

| | | | |
|---|---|---|---|
| 7,512,298 | B2 | 3/2009 | Yi et al. |
| 2003/0044155 | A1 | 3/2003 | Maiden |
| 2007/0258691 | A1* | 11/2007 | Charters et al. ............... 385/132 |
| 2008/0282741 | A1* | 11/2008 | Shimizu et al. ................. 65/386 |

FOREIGN PATENT DOCUMENTS

| | | |
|---|---|---|
| JP | 2001-291265 | 10/2001 |
| JP | 2010-511871 | 4/2010 |

OTHER PUBLICATIONS

Ghaffari, A., et al., "Transfer of micro and nano-photonic silicon nanomembrane, waveguide devices on flexible substrates," Optics Express vol. 18 (19):20086, Optical Society of America, United States (Sep. 2010).

Byun, K.Y., et al., "Single-Crystalline Silicon Layer Transfer to a Flexible Substrate Using Wafer Bonding," Journal of Electronic Materials vol. 39 (10):2233-2236, The Minerals, Metals & Materials Society, United States (Jun. 2010).

Kaiser, K., "Herstellung eines hochelastischen Tuben-endoskops aus Silikon," Hamburger Studententag zur Medizin- und Biotechnologie, 7:16-17, Germany (May 2010).

International Search Report mailed Jun. 5, 2013, directed to Application No. PCT/EP2013/052387, filed on Feb. 7, 2013; 4 pages.

Translation of Japanese Office Action mailed Feb. 3, 2015, directed to Application No. 2014-556045; 4 pages.

\* cited by examiner

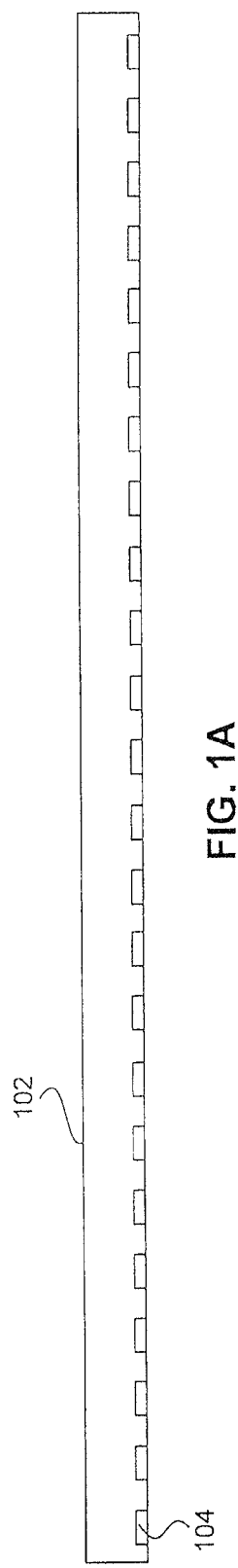
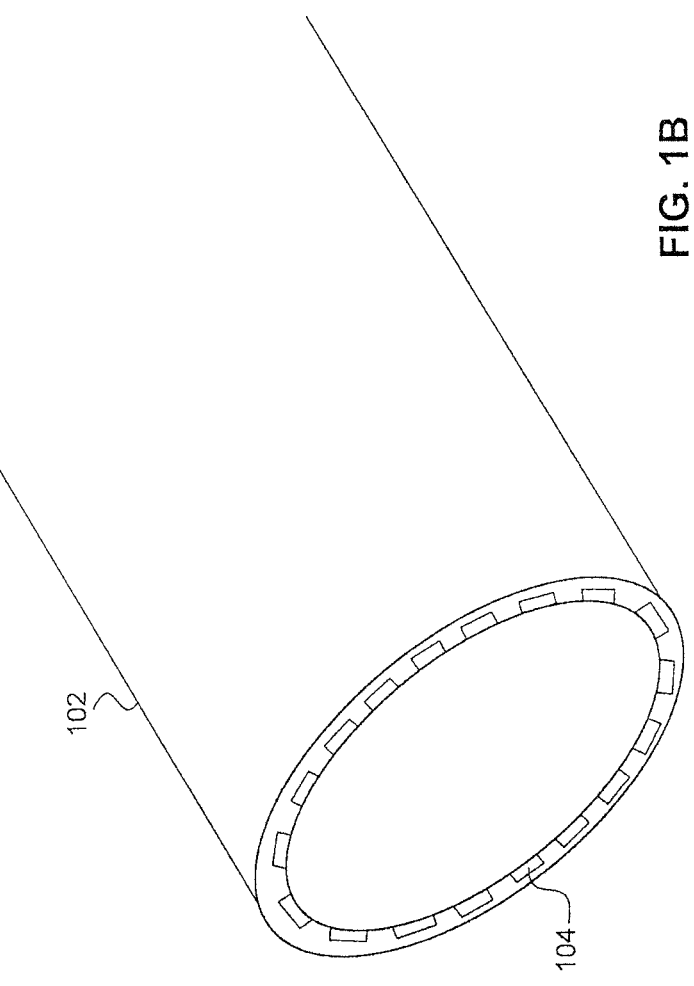

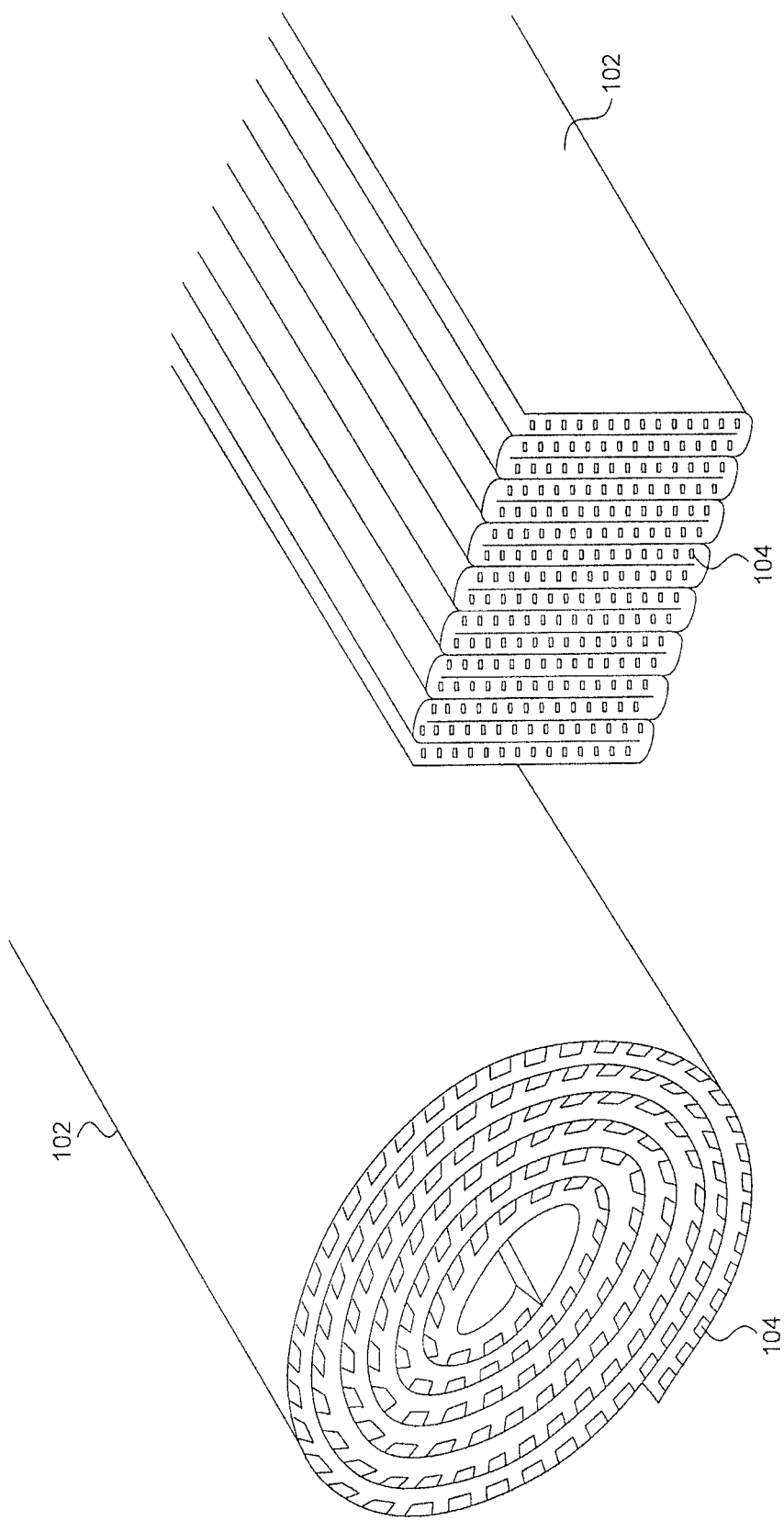

FLEXIBLE WAVEGUIDES FOR OPTICAL COHERENCE TOMOGRAPHY

CROSS REFERENCE TO RELATED APPLICATIONS

This application is a continuation of U.S. application Ser. No. 13/761,054 filed Feb. 6, 2013, which claims the benefit under 35 U.S.C. §119(e) of U.S. provisional patent application Ser. No. 61/596,085, filed Feb. 7, 2012, the disclosures of which are incorporated by reference herein in their entireties.

BACKGROUND

1. Field

Embodiments described herein relate to the field of optical coherence tomography.

2. Background

Optical coherence tomography (OCT) is an imaging technique employed to view layers at different depths of a sample. The layers can be combined to create a three-dimensional map of the sample's surface and depth up to a few millimeters. OCT imaging systems commonly collect information of the sample's structure on a line-by-line basis. Each line scan (also called an A-scan) provides one-dimensional in-depth information from a region of the sample. By scanning the light beam laterally across the sample and then grouping several A-scans, two- and three-dimensional models can be formed of the sample. The scanning is traditionally carried out by mechanical movement of an optical element.

SUMMARY

Embodiments herein describe the use of a flexible substrate comprising a plurality of waveguides to be used with an OCT system.

In an embodiment, a system for depth-resolved imaging of a sample includes a substrate of substantially flexible material, a plurality of waveguides disposed on the substrate, an optical element disposed at a distal end of the plurality of waveguides, and one or more interferometers configured to combine a reference light with light received by at least a portion of the plurality of waveguides to resolve contributions from a given depth of the sample. The system further includes a light guiding element coupled between the plurality of waveguides and the one or more interferometers.

In another embodiment, a system for depth-resolved imaging of a sample includes a substrate of substantially flexible material, a plurality of waveguides disposed on the substrate, an optical element disposed at a distal end of the plurality of waveguides, and one or more interferometers configured to combine a reference light with light received by at least a portion of the plurality of waveguides to resolve contributions from a plurality of depths of the sample. The system further includes a light guiding element coupled between the plurality of waveguides and the one or more interferometers.

An example method of making an optical coherence tomography system includes bonding a layer of semiconducting material to a layer of flexible material. The layer of semiconducting material is further thinned to a thickness of less than 10 microns. The method includes patterning the layer of semiconducting material to form a plurality of waveguides bonded to the layer of flexible material. The method also includes bending the layer of flexible material having the plurality of waveguides bonded thereto and coupling the plurality of waveguides on the bent flexible material to one or more interferometers used to perform optical coherence tomography.

Another example method of making an optical coherence tomography system includes patterning a layer of semiconducting material in a device layer of a SOI wafer to form a plurality of waveguides and depositing a first layer of flexible material over the plurality of waveguides formed in the device layer. The SOI wafer includes a layer structure having the device layer, a buried oxide layer, and a handle layer. The handle layer is etched to substantially remove the handle layer followed by etching the buried oxide layer to substantially remove the buried oxide layer. A second layer of flexible material is deposited over the plurality of waveguides such that the plurality of waveguides are sandwiched between the first and second layers of flexible material to form a flexible optical circuit. The method further includes bending the flexible optical circuit and coupling the plurality of waveguides on the bent flexible optical circuit to one or more interferometers used to perform optical coherence tomography.

BRIEF DESCRIPTION OF THE DRAWINGS/FIGURES

The accompanying drawings, which are incorporated herein and form a part of the specification, illustrate embodiments of the present invention and, together with the description, further serve to explain the principles of the invention and to enable a person skilled in the pertinent art to make and use the invention.

FIGS. 1A-D illustrate a plurality of waveguides on a flexible substrate and examples of bending the substrate, according to embodiments.

FIGS. 2A-D illustrate various views of the end of a catheter, according to embodiments.

DETAILED DESCRIPTION

Figure 2A:
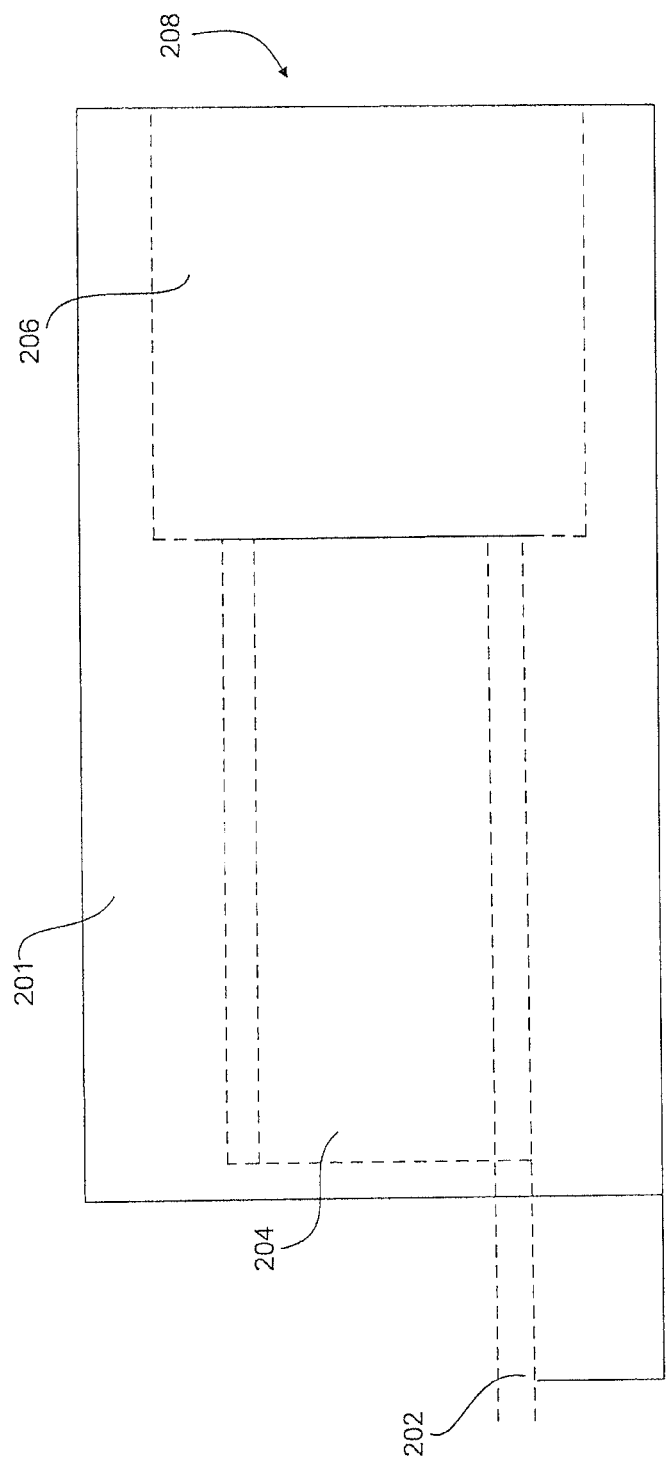

Although specific configurations and arrangements are discussed, it should be understood that this is done for illustrative purposes only. A person skilled in the pertinent art will recognize that other configurations and arrangements can be used without departing from the spirit and scope of the present invention. It will be apparent to a person skilled in the pertinent art that this invention can also be employed in a variety of other applications.

It is noted that references in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure or characteristic is described in connection with an embodiment, it would be within the knowledge of one skilled in the art to effect such feature, structure or characteristic in connection with other embodiments whether or not explicitly described.

Overcoming the need for mechanical movement in an OCT scanner can be realized by using a large number of optical waveguides to collect light from multiple points on a sample.

Waveguides have previously been fabricated in a planar lightwave circuit (PLC). The PLC may further include active elements to switch the path of the light between different waveguides or modulate the frequency of the light. However, waveguides fabricated in a PLC are, by definition, coplanar. This hinders the use of a PLC-based OCT system for applications which require radial or conical scanning (such as endoscopy). Furthermore, common endoscopic or catheter probes can be smaller than 3 mm which limits the number of useable waveguides along the edge of a PLC.

In an embodiment of the present invention, the waveguides are provided on a flexible substrate. The flexible substrate allows for the waveguides to be curled or bent into various shapes and more efficiently fill a given area. For example, the flexible substrate may be curled into a tight spiral or layered in an accordion-type shape. Once the flexible substrate has been manipulated into a particular form, it may be placed into a housing or any other type of packaging for protection and to help the substrate maintain its shape. For example, the flexible substrate may be curled and subsequently placed into the cylindrical housing of an endoscope to provide a dense array of waveguides within the housing.

FIG. 1A illustrates an example of a flexible substrate 102 comprising a plurality of waveguides 104. The flexible substrate may be a polymer such as, for example and without limitation, polydimethylsiloxane (PDMS) or Parylene. The flexible substrate may also be a thin semiconductor material. Flexible substrate 102 may be sufficiently flexible so as to roll or bend without tearing.

Flexible substrate 102 is configured to adapt to various shapes as may be useful for different applications. Once implemented onto flexible substrate 102, waveguides 104 can then be arranged in a non-coplanar fashion while still allowing for focusing optics to direct the light coming out of the different waveguides 104 according to any desired sampling pattern.

Waveguides 104 may be made from a single polymer material, or may include a combination of polymer materials. For example, waveguides 104 may be made from any one of SU-8, PMMA, PDMS, etc. Waveguides 104 may also be made from a semiconductor material such as silicon, or III-V semiconductor materials such as gallium arsenide or indium phosphide. It should be understood that impurities or other material combinations may exist in the semiconductor materials, for example, tertiary or quaternary compounds.

Waveguides 104 may be fabricated on the surface of flexible substrate 102. Surface patterning may involve a variety of lithographic masking and etching techniques. Some examples of etching techniques include reactive ion etching, inductive coupled plasma etching, and wet chemical etching. In another embodiment, waveguides 104 may be formed via bulk micromachining in which the material of waveguides 104 is bonded to flexible substrate 102 and subsequently thinned to a final thickness below 100 microns. Smaller single-mode or nearly single-mode waveguides may be thinned to a final thickness below 10 microns or below 1 micron. In one embodiment, the final thickness of waveguides 104 is about 3 microns. Examples of thinning procedures include chemical mechanical polishing, bulk wet etching, and etching using a reactive gas such as xenon difluoride. Structural integrity may be ensured through the introduction of carrier layers with appropriate tensile strength yet sufficient flexibility. Other wafer-level substrate transfer processes can be used to transfer waveguides formed as an optical device layer onto films such as substrate 102, as would be understood by one of skill in the art.

In another example, waveguides 104 may be embedded within flexible substrate 102. Embedding waveguides 104 may provide better optical mode containment within the waveguide due to the same or similar cladding material surrounding each waveguide. Substrate 102 may be layered around waveguides 104 in order to embed waveguides 104. In another example, waveguides 104 may be doped regions of a semiconductor layer with a top semiconductor layer deposited over the doped layer to embed waveguides 104. The semiconductor layers may be epitaxially grown or deposited using chemical vapor deposition techniques.

Waveguides 104 may be disposed on or within substrate 102 such that all of the waveguides are parallel to each other. When waveguides 104 are disposed onto a layer of a semiconductor or plastic substrate, they can create a flexible optical integrated circuit.

FIGS. 1B-D illustrate various ways that one may bend substrate 102 into different shapes. FIG. 1B shows substrate 102, containing embedded waveguides 104, as rolled into a cylindrical shape. FIG. 1C shows substrate 102 rolled into itself to create a spiral pattern of waveguides 104. FIG. 1D shows substrate 102 folded to create a layered pattern. The circular and the spiral arrangement of substrate 102 are useful when circular or conical scanning is required. FIGS. 1C and 1D may be particularly useful when dense three-dimensional scanning patterns are desired. Other shapes may be considered as well without deviating from the scope or spirit of the invention.

Such a combination of waveguides and flexible substrate, when bent, can be combined with active elements to switch a light beam from one waveguide to another. In such a manner, scanning may be performed without the need for mechanical scanning means. The active elements may be based on electro-optic, thermo-optic, or carrier injection effects, for instance. In combination with terminal optics which focus the light coming out of each waveguide onto a different point of the sample's surface, an akinetic (without any moving parts) scanning system for OCT imaging can be achieved.

Waveguides defined inside traditional PLCs are, by definition, coplanar. This would hinder the use of an akinetic PLC-based scanning system for some applications, such as endoscopic or catheter-based OCT systems, where special sample scanning schemes (e.g., radial scanning or conical scanning) are needed. Line scanners are generally inefficient for obtaining radial or conical image information. The reason is that the optical focusing system needed to convert the light beams from an array of co-planar waveguides in a PLC into a complex scanning pattern on the tissue is challenging to implement. In order to solve this problem, a system may use a flexible waveguide system such as the embodiments described with respect to FIGS. 1A-1D.

FIGS. 2A-D provide various views of the end of a catheter or endoscope which includes a flexible waveguide system, according to an embodiment. Elements shown in broken lines are illustrated as being within housing 201.

FIG. 2A illustrates a side view of a probe which includes a housing 201, a light guiding element 202, a flexible waveguide system 204, and an optical element 206 disposed at distal end 208 of the probe. Light guiding element 202 may be, for example, a single optical fiber or a bundle of fibers. Alternatively, light guiding element 202 may be a planar waveguide fabricated on a substrate. In one example, light guiding element 202 is a waveguide fabricated on the same flexible substrate as included in flexible waveguide system 204.

Flexible waveguide system 204 may include a plurality of waveguides similar to substrate 102 as described in FIGS.

1A-D. Additionally, flexible waveguide system 204 may be rolled into a cylindrical or spiral shape, for example. In an embodiment, a diameter of distal end 208 of housing 201 is less than 3 mm. In another example, the diameter of distal end 208 is less than 1 mm.

Optical element 206 directs light coming out of flexible waveguide system 204 onto a sample, according to an embodiment. Optical element 206 may be, for example, any number of lenses and/or mirrors designed to guide light exiting distal end 208 towards a sample to be imaged. Optical element 206 may also be designed to collect light scattered back off of the sample. In one embodiment, optical element 206 includes at least one lens that is a gradient index (GRIN) lens. In another example, optical element 206 includes one or more spherical lens components. Distal end 208 may additionally or alternatively include a mirror to direct the light at a specific angle as it exits from distal end 208. Such a mirror may also be used for collecting light at a specific angle off of the sample. Such a mirror may be a static mirror or a moveable mirror.

Light guiding element 202 is configured to transmit light between flexible waveguide system 204 and other optical components not disposed within housing 201, according to an embodiment. In another example, other optical components are coupled directly with flexible waveguide system 204 within housing 201. These other optical components may include electrical or thermal modulators to change the frequency of the light. Other optical components may also include one or more interferometers to constructively and/or destructively interfere the light. The interferometers may be utilized for performing either time or frequency domain optical coherence tomography.

Although only one light guiding element 202 is illustrated, it should be understood that any number of light guiding elements may be used to guide light from various waveguides within flexible waveguide system 204 to other optical components of the system. Alternatively, one or more optical switches may be utilized to switch to a particular waveguide of the plurality of waveguides in flexible waveguide system 204 to couple light into light guiding element 202.

Figure 2B:
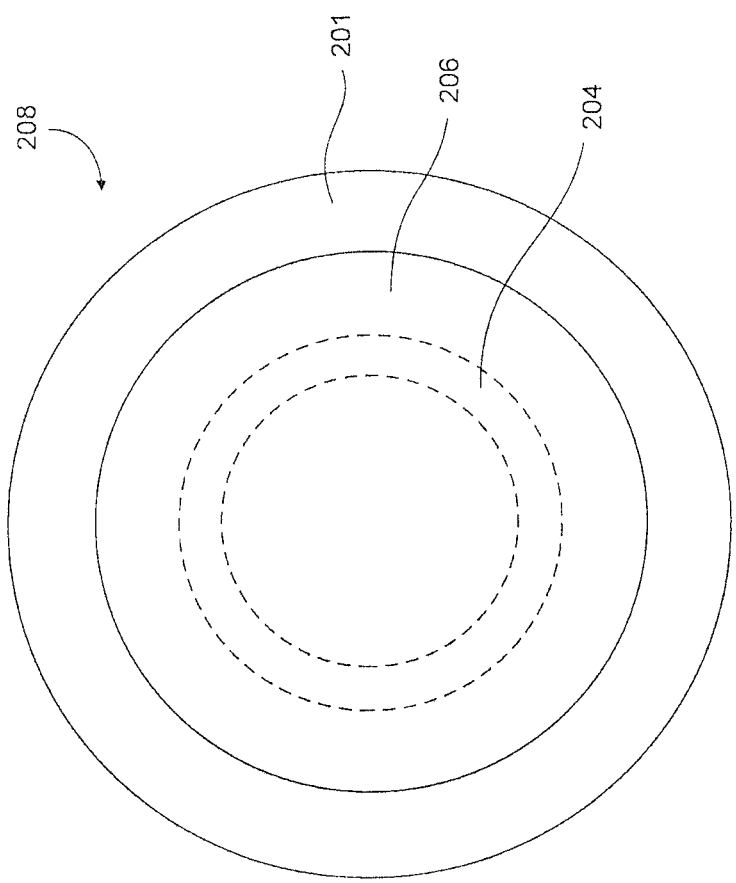

FIG. 2B illustrates a front view looking into distal end 208 of the probe, according to an embodiment. Optical element 206 may fill the region at distal end 208. As such, flexible waveguide system 204 is shown behind optical element 206 using broken lines. Flexible waveguide system 204 is wrapped in a tube-like shape, according to an embodiment.

Figure 2C:
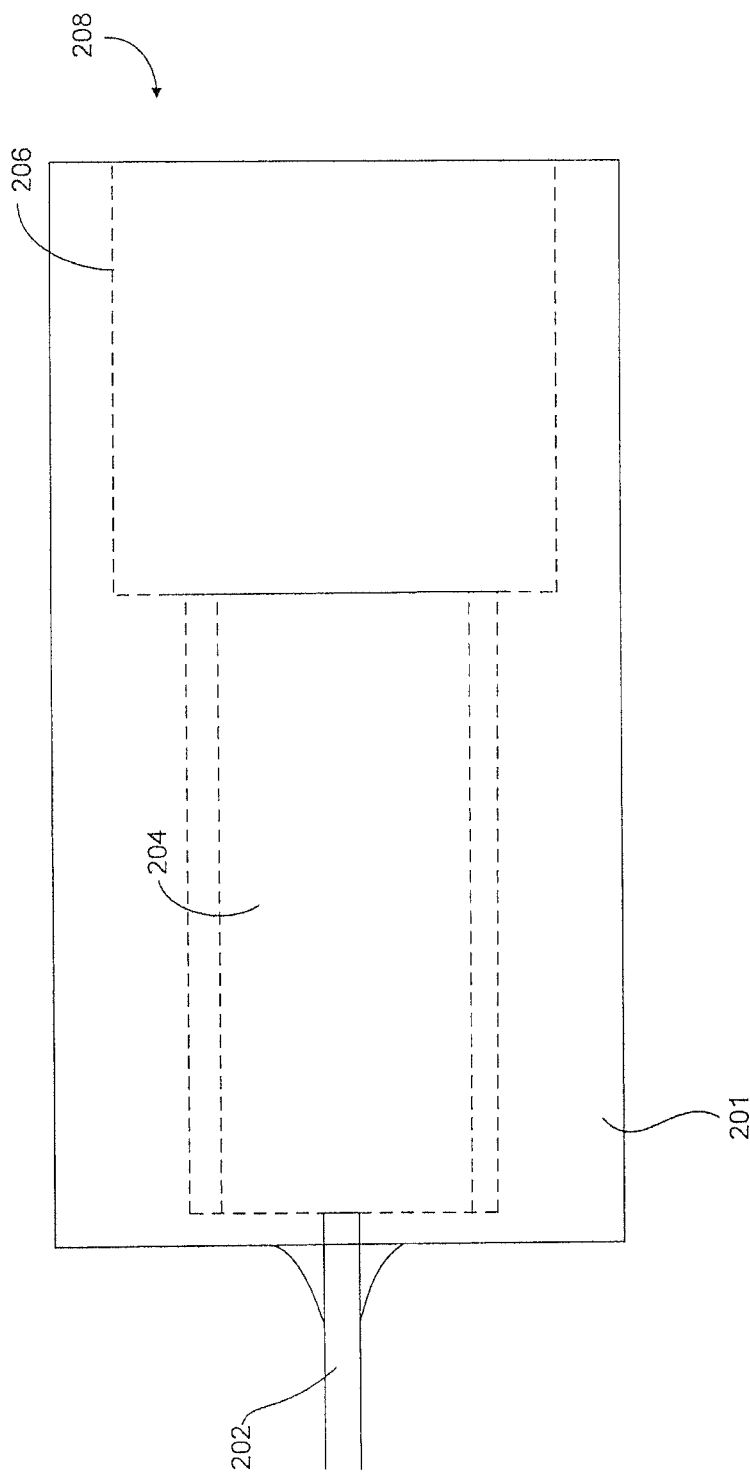

FIG. 2C illustrates a top view of the probe that includes flexible waveguide system 204 and optical element 206 within housing 201, according to an embodiment. Light guiding element 202 can be seen connecting to flexible waveguide system 204 within housing 201.

Figure 2D:
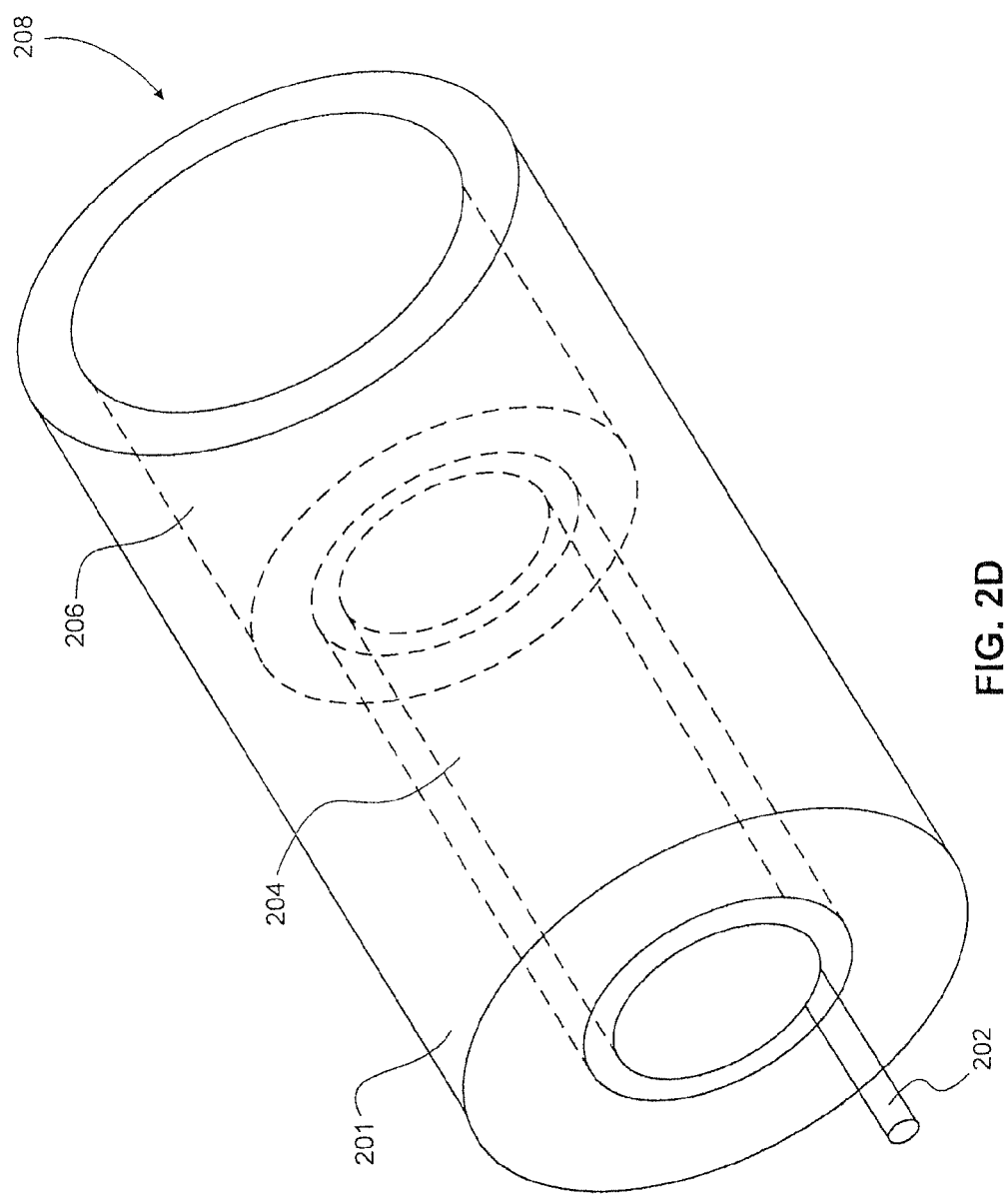

FIG. 2D illustrates a perspective view of the probe end. A cylindrical shape of flexible waveguide system 204 disposed within the cylindrical housing 201 of the probe is observed, according to an embodiment. Light guiding element 202 may be coupled to a portion of flexible waveguide system 204, according to an embodiment, or it may be coupled to all waveguides in flexible waveguide system 204. A single light guiding element 202 is illustrated; however, a plurality of light guiding elements may be disposed around substantially the entire circumference of flexible waveguide system 204 to capture light from the waveguides of flexible waveguide system 204.

Another optical element may be used to direct the light from light guiding element 202 to one or more of the waveguides on flexible waveguide system 204. For example, a multiplexer may be disposed between light guiding element 202 and flexible waveguide system 204. In another example, the multiplexer is disposed on the substrate of flexible waveguide system 204. The multiplexer may include one or more of optical switches, circulators, beam steering modulators, etc. The multiplexer allows for the integration of many optical paths via flexible waveguide system 204 with a single optical path via light guiding element 202.

Figure 3:
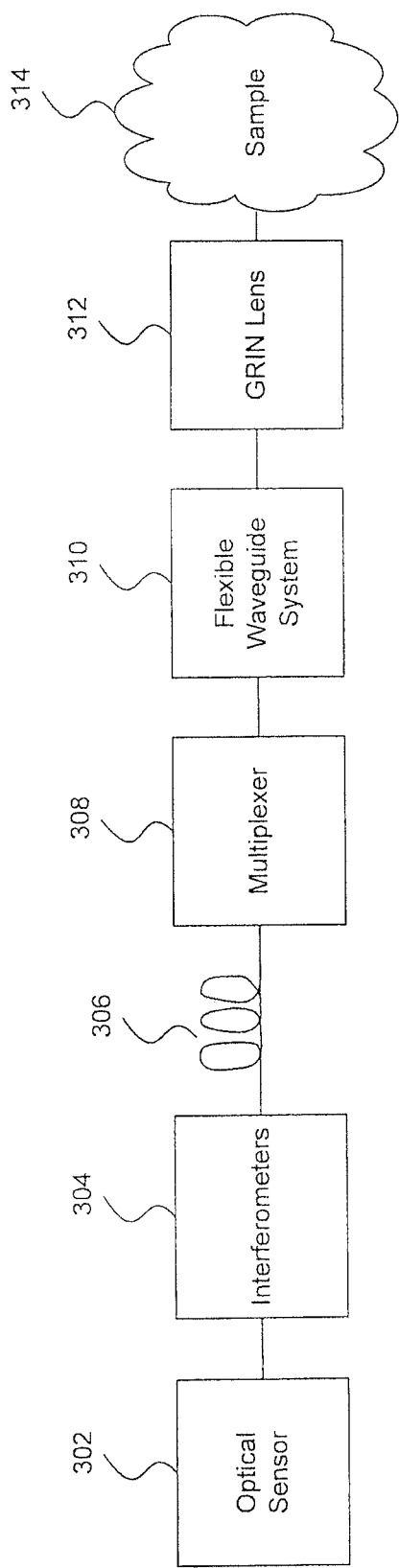
FIG. 3 illustrates a block diagram of an OCT system, according to an embodiment.

FIG. 3 illustrates a diagram of an example OCT system 300 which includes the use of a flexible waveguide system, according to an embodiment. OCT system 300 includes an optical sensor 302, one or more interferometers 304, a light guiding element 306 which couples interferometers 304 to a multiplexer 308, a flexible waveguide system 310, and an optical element 312. In the example illustrated in FIG. 3, optical element 312 is a GRIN lens. Not shown in FIG. 3 is a light source which would produce light to be directed onto a sample 314 at some distance from optical element 312. The light produced from the light source may also be directed down light guiding element 306 and through flexible waveguide system 310 on its way to sample 314. In an embodiment, the light source may also be used as a reference light.

In one embodiment, one or more interferometers 304 are used to perform time domain optical coherence tomography (TD-OCT). The optical path length of a reference arm of the one or more interferometers 304 is modulated so as to modulate a reference beam of light. When the modulated reference beam is combined with a beam of light received from sample 314, the resulting interference resolves signal contributions from a given depth of sample 314. The optical path length of the reference arm may be changed over time to yield image data at different depths of sample 314. The modulation of the optical path length is traditionally performed by mechanically moving one or more mirrors in the path of the reference light beam. However, other modulation techniques are to be considered as well, such as, for example, thermo-optic or electro-optic modulators coupled to a waveguide for altering the optical path length of the light within the waveguide.

In another embodiment, one or more interferometers 304 are used to perform frequency domain optical coherence tomography (FD-OCT). When performing FD-OCT, multiple depths of sample 314 may be analyzed substantially simultaneously by, for example, using a plurality of spectrally separated detectors at optical sensor 302. A Fourier transform may be performed on the signal received by optical sensor 302 to resolve various signal components associated with various depths of sample 314. In one example, performing FD-OCT allows for acquiring image information at various depths without the need for changing the optical path length of the reference arm in the one or more interferometers 304.

Multiplexer 308 may be configured to transmit light through a first subset of waveguides on flexible waveguide system 310 while receiving light scattered back from sample 314 from a second subset of waveguides on flexible waveguide system 310. As light is reflected back from sample 314 into optical element 312, it travels back along light guiding element 306 to one or more interferometers 304, according to one embodiment. In another example, the light may travel back to one or more interferometers 304 using a different path than via light guiding element 306. One or more interferometers 304 may combine the light with a reference light to constructively and/or destructively interfere the light. The resolved light associated with either a given depth of sample 314 when performing TD-OCT, or a plurality of depths of sample 314 when performing FD-OCT, is collected at optical sensor 302.

Sample 314 may be a tissue sample, for example, a lining of a heart or a colon. A plurality of locations on sample 314 may be imaged at one time due to the plurality of waveguides present in flexible waveguide system 310. Additionally, radial and/or conical image information may be collected from sample 314 due to the circular arrangement of waveguides.

Figure 4:
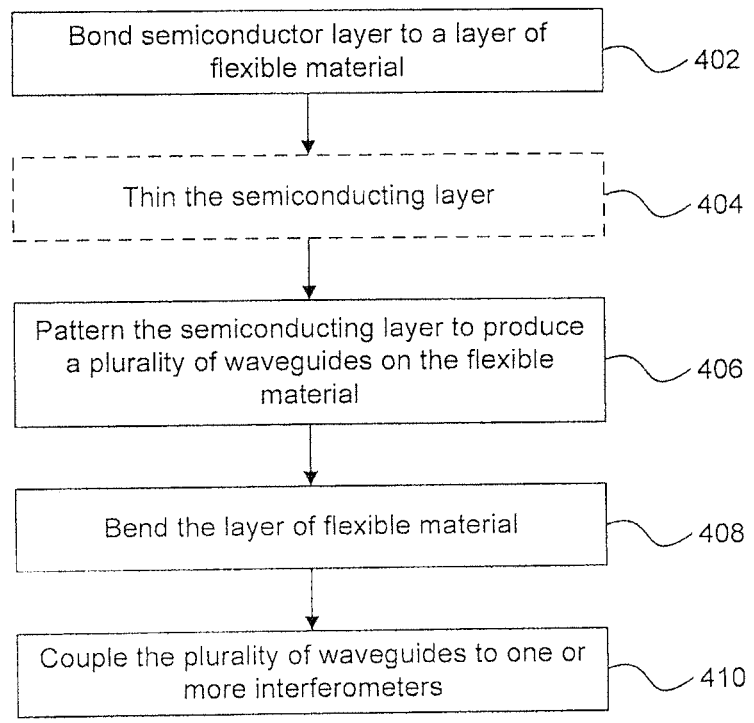
FIG. 4 illustrates an example method, according to an embodiment.

FIG. 4 illustrates a flowchart depicting a method 400 for fabricating an optical coherence tomography system, according to an embodiment of the invention. The fabrication of the system may involve fabricating a plurality of waveguides on a flexible material such as those illustrated, for example, in FIGS. 1B-1D. It is to be appreciated that method 400 may include operations additional to those shown, or perform the operations in a different order than shown.

Method 400 begins at step 402 where a semiconductor layer is bonded to a layer of flexible material, according to an embodiment. The semiconductor may be, for example, silicon or gallium arsenide. The flexible material may be, for example, PDMS or Parylene. The bonding may be anodic, or may use other techniques as would be known by one skilled in the relevant art(s) given the description herein.

Method 400 continues with step 404 where the semiconductor layer is thinned. The thinning may produce a semiconductor layer having a thickness of less than 10 microns. In one embodiment, the final thickness of the semiconductor layer is around 3 microns. Chemical mechanical polishing (CMP) may be utilized for the thinning procedure. It should be understood that step 404 may not be necessary in a case where the semiconductor layer is already thin enough when initially bonded to the flexible material.

In step 406, the semiconductor layer is patterned to form waveguides on the flexible material, according to an embodiment. The patterning of the semiconductor layer may involve conventional lithography techniques to first pattern a photoresist layer over the semiconductor layer and subsequently etch the exposed semiconductor material to form the waveguides. Alternatively, a hard mask material such as silicon nitride may be used in place of photoresist. In one embodiment, the waveguides are formed as substantially parallel lines on the flexible material. After the waveguides are formed, a cladding material may be deposited or added over the top of the waveguides to further confine the light mode within the waveguide core.

In step 408, the layer of flexible material having the plurality of waveguides is bent into a particular shape, according to an embodiment. In one example, the flexible material may be bent into a cylindrical or spiral shape as illustrated in FIGS. 1B and 1C respectively. A generally circular shape may aid the placement of the flexible waveguides into a tubular-like apparatus such as a catheter or endoscope. Other shapes may be considered as well to more conveniently place the flexible waveguides into various devices. The various bent shapes of the waveguides can decrease the form factor of an optical system and also provide additional imaging techniques not readily available from strictly co-planar waveguides.

In step 410, the plurality of waveguides are coupled to one or more interferometers, according to an embodiment. The one or more interferometers combine the light received from at least a portion of the plurality of waveguides with a reference beam of light to perform OCT imaging. The coupling between the waveguides and the interferometers may involve any number of light guiding elements, lenses, mirrors, multiplexers etc. For example, a light guiding element, such as an optical fiber, may be used to couple light from the plurality of waveguides to the one or more interferometers. In another example, one or more lenses may be used to focus the light exiting from the plurality of waveguides onto a light guiding element, or directly onto an optical element integrated as part of the one or more interferometers.

Figure 5:
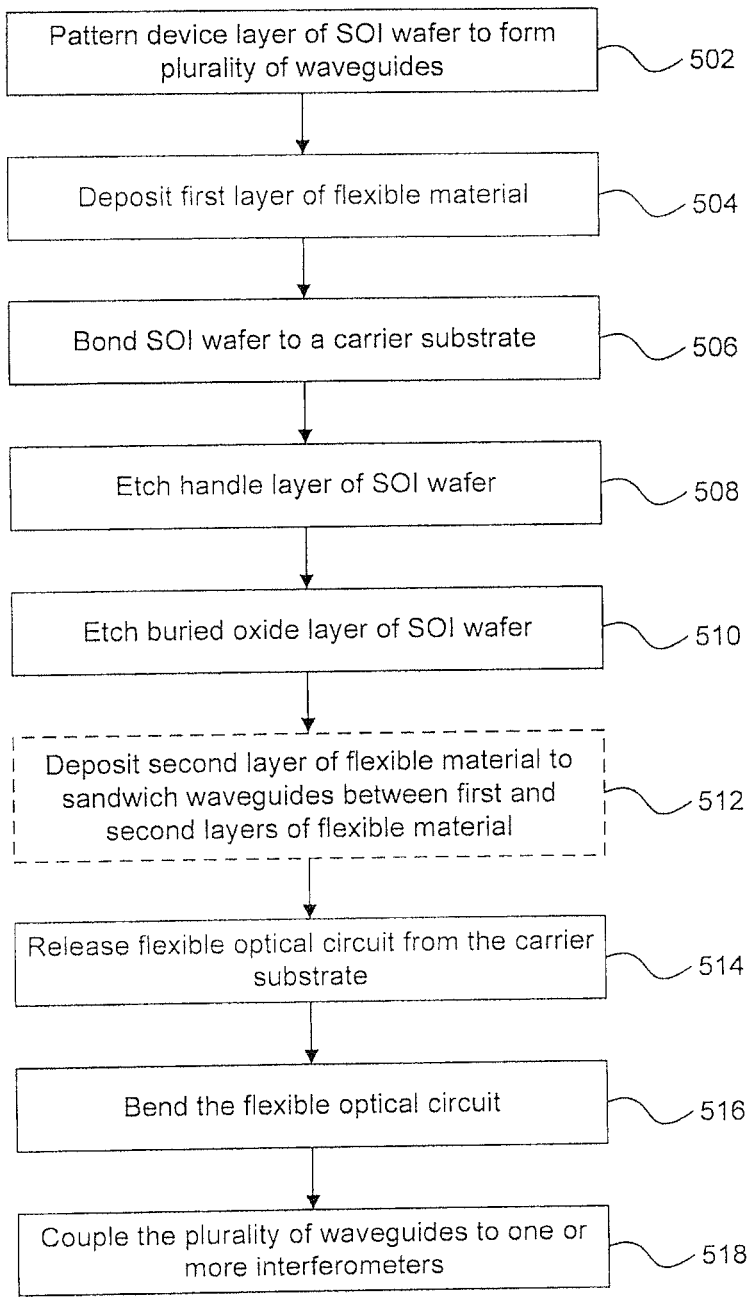
FIG. 5 illustrates an example method, according to an embodiment.

FIG. 5 illustrates a flowchart depicting a method 500 for fabricating an optical coherence tomography system, according to another embodiment of the invention. It is to be appreciated that method 500 may include operations additional to those shown, or perform the operations in a different order than shown.

Method 500 begins at step 502 where a device layer of a Silicon-On-Insulator (SOI) wafer is patterned to form waveguides, according to an embodiment. The SOI wafer may include a semiconducting device layer, a buried silicon dioxide layer, and a handle layer that may be up to several hundred microns thick. It should be appreciated, however, that the SOI wafer and fabrication process described in method 500 should not be limited to using silicon as the device layer, and that other semiconducting and polymer materials could be used as well. As above, the patterning of the semiconductor layer may involve conventional lithography techniques to first pattern a photoresist layer over the semiconductor layer and subsequently etch the exposed semiconductor material to form the waveguides. Alternatively, a hard mask material such as silicon nitride may be used in place of photoresist. In one embodiment, the waveguides are formed as substantially parallel lines on the flexible material. The device layer may have a thickness of, for example, less than 10 microns. In one embodiment, the final thickness of the device layer is around 3 microns. After the waveguides are formed, a cladding material may be deposited or added over the top of the waveguides to further confine the light mode within the waveguide core. Other material layers or process steps could be added for additional electrical or optical functionality.

Method 500 continues at step 504, where a thin layer of flexible material is deposited on top of the SOI wafer ensuring good adhesion to the device layer where the waveguides have been defined, according to an embodiment. The flexible material may be, for example, PDMS or Parylene. Deposition will be done through spinning, layer transfer based on temperature and pressure application or other methods known by one skilled in the relevant art(s) given the description herein. Adhesion between the flexible material and the device layer where the waveguides have been defined may be ensured through surface preparation using $O_2$ plasma or other means, such as, for example, intermediate adhesion promotion layers. Other techniques for improving the adhesion may be used as would be known by one skilled in the relevant art(s) given the description herein.

Method 500 continues with step 506 where the SOI wafer with the flexible material on top is attached to a carrier substrate, according to an embodiment. Such attachment may be achieved through a thin adhesive layer, including a photoresist layer. The adhesive may be selected so as to be easily removed with a solvent without adversely affecting the flexible layer or the waveguides. Such a solvent may be, for example, acetone, methanol, isopropanol or any other organic or inorganic solvent.

Method 500 continues with step 508 where the handle layer of the SOI wafer is etched, using the buried oxide layer as a stop layer. This etching step can be done using wet anisotropic etching, wet isotropic etching, deep reactive ion etching, other plasma-based etching processes or other means known by one skilled in the relevant art(s) given the description herein. This etching step can be modulated by a lithography step, where solid silicon islands are protected through a soft or hard mask. Such rigid islands may be left on the buried oxide in as far as this may be needed to strengthen the structure for packaging, functional or other application needs.

In step 510, the buried oxide layer is subsequently etched away using an etching solution, according to an embodiment. In one example, the etching solution may be chosen to have either a zero or negligible etch rate for the waveguide material to protect the waveguides. Such an etchant may be based on hydrofluoric acid (HF), but other compositions are possible as would be known to one skilled in the relevant art(s).

In step 512, another flexible layer is deposited on the exposed silicon waveguides, according to an embodiment. Step 512 is optional, however, the additional flexible layer sandwiches the waveguides in order to protect the optical circuit, add additional mechanical strength, and improve the cladding around the waveguides. In this step, further patterning of the flexible optical circuit is possible, whereby arbitrary shapes may be defined in the substrate. Such shapes may be used to enhance flexibility, simplify packaging, or other purposes. Patterning may be performed using lithography masks to protect the flexible optical circuit from the etching step. Etching of the flexible optical circuit may be achieved, for example, through plasma-based etching processes.

In step 514, the flexible optical circuit is released from the carrier substrate, according to an embodiment. The release may occur on the die level after cutting the flexible optical circuit bonded to the carrier substrate into dies of adequate size. The release may be performed by using a solvent that dissolves the adhesion layer only.

In step 516, the flexible optical circuit is bent into a particular shape, according to an embodiment. In one example, the flexible optical circuit may be bent into a cylindrical or spiral shape as illustrated in FIGS. 1B and 1C respectively. A generally circular shape may aid the placement of the flexible waveguides into a tubular-like apparatus such as a catheter or endoscope. Other shapes may be considered as well to more conveniently place the flexible waveguides into various devices. The various bent shapes of the waveguides can decrease the form factor of an optical system and also provide additional imaging techniques not readily available from strictly co-planar waveguides.

In step 518, the plurality of waveguides on the flexible material are coupled to one or more interferometers, according to an embodiment. The one or more interferometers combine the light received from at least a portion of the plurality of waveguides with a reference beam of light to perform OCT imaging. The coupling between the waveguides and the interferometers may involve any number of light guiding elements, lenses, mirrors, multiplexers etc. For example, a light guiding element, such as an optical fiber, may be used to couple light from the plurality of waveguides to the one or more interferometers. In another example, one or more lenses may be used to focus the light exiting from the plurality of waveguides onto a light guiding element, or directly onto an optical element integrated as part of the one or more interferometers.

Some embodiments of a flexible waveguide system described herein provide certain structural advantages. For example, waveguides disposed onto a flexible substrate may have a size advantage over standalone optical fibers, in that the waveguides disposed on a substrate can be made much smaller than a standalone fiber because the substrate can be used as structural support for the waveguides. Utilizing smaller waveguides allows for packing more waveguides over a given area. As such, more individual data points may be taken for a given surface area. Further, once the waveguides have been disposed on a substrate, the waveguides may be organized into a specific, stable shape, which may not be possible or easy with standalone optical fibers.

Embodiments of the present invention have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

What is claimed is:

1. An optical coherence tomography system for depth-resolved imaging of a sample, comprising:
a substantially flexible polymer substrate bonded to a layer of semiconducting material, wherein the layer of semiconducting material is patterned to form a plurality of waveguides, and wherein the substrate is bent;
an optical element disposed at a distal end of the plurality of waveguides;
one or more interferometers configured to combine a reference light with light received by at least a portion of the plurality of waveguides on the bent substrate to resolve contributions from a given depth of the sample using optical coherence tomography; and
a light guiding element coupled between the plurality of waveguides on the bent substrate and the one or more interferometers.

2. The system of claim 1, wherein the polymer substrate comprises PDMS.

3. The system of claim 1, wherein the polymer substrate comprises parylene.

4. The system of claim 1, wherein the plurality of waveguides are composed of at least one of silicon, gallium arsenide, and indium phosphide.

5. The system of claim 1, further comprising an optical multiplexer configured to switch a path of light from the light guiding element to one or more of the plurality of waveguides.

6. The system of claim 1, wherein the substrate is configured to be rolled into a substantially cylindrical shape.

7. The system of claim 6, wherein the substrate is disposed within a substantially cylindrical housing.

8. The system of claim 1, wherein the optical element comprises one or more mirrors.

9. The system of claim 1, wherein the optical element comprises one or more lenses.

10. The system of claim 9, wherein at least one of the one or more lenses is a gradient index lens.

11. The system of claim 1, wherein the light guiding element is an optical fiber.

12. The system of claim 1, wherein the plurality of waveguides comprise single-mode waveguides.

13. An optical coherence tomography system for depth-resolved imaging of a sample, comprising:
   a substantially flexible polymer substrate bonded to a layer of semiconducting material, wherein the layer of semiconducting material is patterned to form a plurality of waveguides, and wherein the substrate is bent;
   an optical element disposed at a distal end of the plurality of waveguides;
   one or more interferometers configured to combine a reference light with light received by at least a portion of the plurality of waveguides on the bent substrate to resolve contributions from a plurality of depths of the sample using optical coherence tomography; and
   a light guiding element coupled between the plurality of waveguides on the bent substrate and the one or more interferometers.

14. The system of claim 13, further comprising an optical multiplexer configured to switch a path of light from the light guiding element to one or more of the plurality of waveguides.

15. The system of claim 13, wherein the substrate is configured to be rolled into a substantially cylindrical shape.

16. The system of claim 15, wherein the substrate is disposed within a substantially cylindrical housing.

17. The system of claim 13, wherein the depth-resolved imaging includes optical coherence tomography (OCT).

18. The system of claim 13, wherein the plurality of waveguides comprise single-mode waveguides.

19. The system of claim 1, wherein each waveguide in the plurality of waveguides has a thickness between 1 and 10 microns.

20. The system of claim 13, wherein each waveguide in the plurality of waveguides has a thickness between 1 and 10 microns.

* * * * *